(12) United States Patent
Yamashita et al.

(10) Patent No.: US 8,758,239 B2
(45) Date of Patent: Jun. 24, 2014

(54) BIOLOGICAL INFORMATION DETECTOR AND BIOLOGICAL INFORMATION MEASURING DEVICE

(75) Inventors: Hideto Yamashita, Nagano (JP); Yoshitaka Iijima, Nagano (JP); Shigemi Sato, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 392 days.

(21) Appl. No.: 12/973,259

(22) Filed: Dec. 20, 2010

(65) Prior Publication Data

US 2011/0166456 A1   Jul. 7, 2011

(30) Foreign Application Priority Data

Jan. 5, 2010   (JP) ................................. 2010-000453

(51) Int. Cl.
*A61B 5/00* (2006.01)
(52) U.S. Cl.
USPC ........... 600/300; 600/324; 600/344; 600/476; 600/479; 600/503
(58) Field of Classification Search
USPC .......................... 600/324, 344, 500, 502, 503
See application file for complete search history.

(56) References Cited

U.S. PATENT DOCUMENTS

| 6,631,282 B2 * | 10/2003 | Rule et al. ...................... 600/344 |
| 7,299,080 B2 * | 11/2007 | Acosta et al. .................. 600/316 |
| 2005/0253047 A1 | 11/2005 | Maegawa et al. |

FOREIGN PATENT DOCUMENTS

| JP | 56-156138 A | 12/1981 |
| JP | 2004-337605 A | 12/2004 |
| JP | 2005-323906 A | 11/2005 |

* cited by examiner

*Primary Examiner* — Navin Natnithithadha
*Assistant Examiner* — Etsub Berhanu
(74) *Attorney, Agent, or Firm* — Global IP Counselors, LLP

(57) ABSTRACT

A biological information detector includes a light-emitting part subjected to emit a first light directed at a detection site of a test subject and a second light directed in a direction other than a direction of the detection site, a first reflecting part subjected to reflect the second light and directing the second light towards the detection site, a light-receiving part subjected to receive light having biological information, where the light produced by the first light and the second light is reflected at the detection site, and a second reflecting part subjected to reflect the light having biological information from the detection site and directing the light having biological information towards the light-receiving part.

14 Claims, 7 Drawing Sheets

(A)
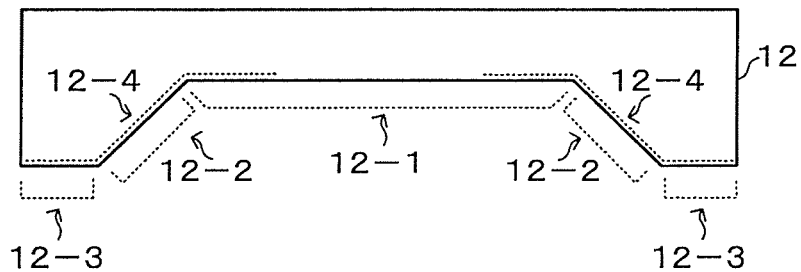
(B)
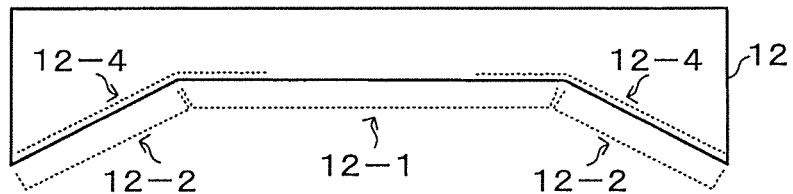
(C)
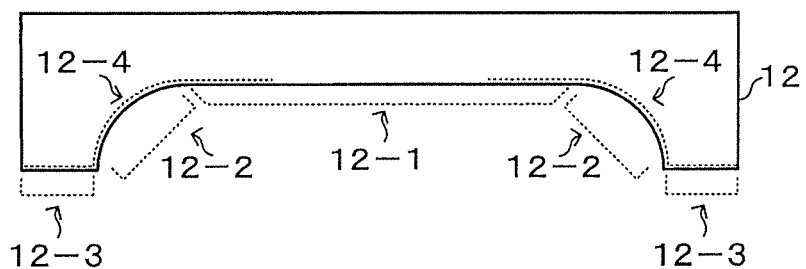
Fig. 2

(A)
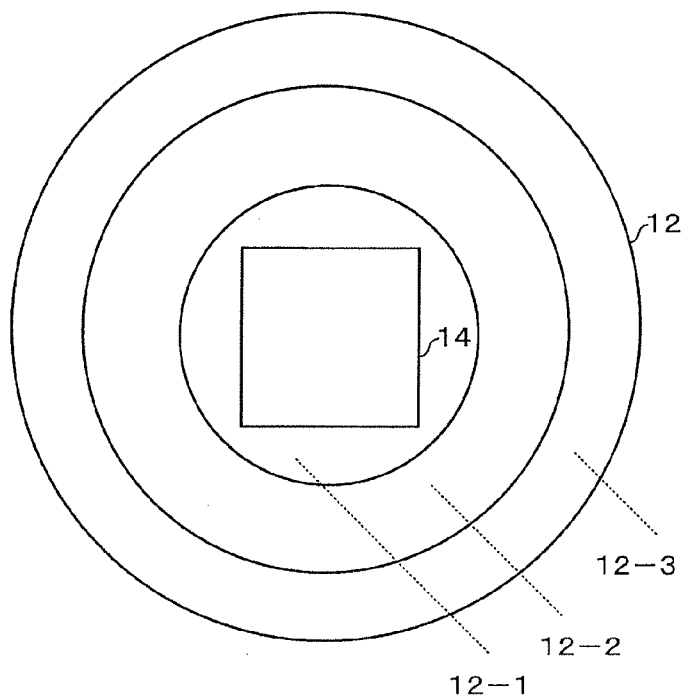
(B)
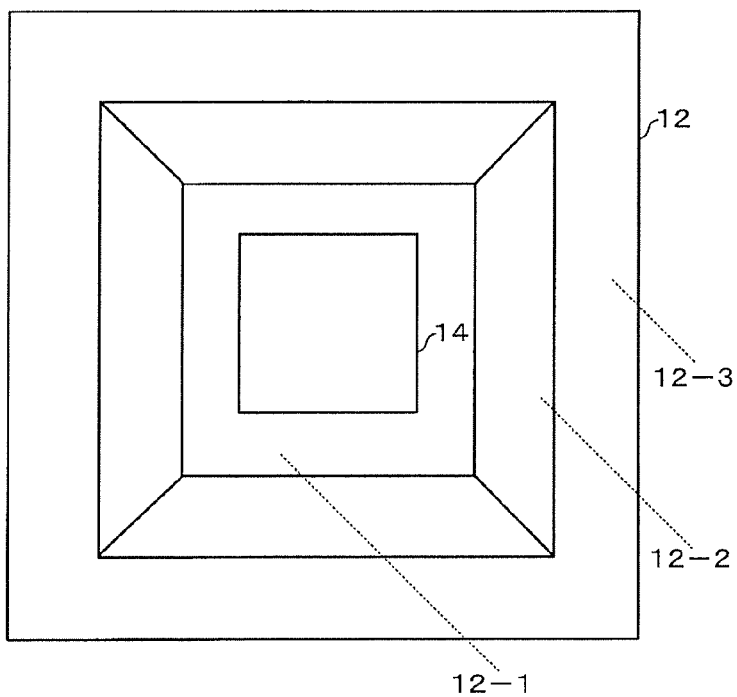
Fig. 3

BIOLOGICAL INFORMATION DETECTOR AND BIOLOGICAL INFORMATION MEASURING DEVICE

BACKGROUND

1. Technological Field

The present invention relates to a biological information detector and a biological information measuring device and similar devices.

2. Background Technology

A biological information measuring device measures human biological information such as, for example, pulse rate, blood oxygen saturation level, body temperature, or heart rate, and an example of a biological information measuring device is a pulse rate monitor for measuring the pulse rate. Also, a biological information measuring device such as a pulse rate monitor may be installed in a clock, a mobile phone, a pager, a PC, or another electrical device, or may be combined with the electrical device. The biological information measuring device has a biological information detector for detecting biological information, and the biological information detector includes a light-emitting part for emitting light towards a detection site of a test subject (e.g. a user), and a light-receiving part for receiving light having biological information from the detection site.

In Patent Citation 1, there is disclosed a pulse rate monitor (or in a broader sense, a biological information measuring device). A light-receiving part (e.g. a light-receiving part 12 in FIG. 16 of Patent Citation 1) of the pulse rate monitor receives light reflected at a detection site (e.g. dotted line in FIG. 16 of Patent Citation 1) via a diffusion reflection plane (e.g. reflecting part 131 in FIG. 16 of Patent Citation 1). In an optical probe 1 in Patent Citation 1 (or in a broader sense, a biological information detector), a light-emitting part 11 and the light-receiving part 12 overlap in plan view, and the size of the optical probe is reduced.

PRIOR ART REFERENCE

Patent Citation

Patent Citation 1: JP-A 2004-337605 is an example of related art.

SUMMARY

Problems to be Solved by the Invention

In the optical probe 1 of Patent Citation 1, in an instance in which there is a significant level of noise arising from to e.g. external light, or under similar circumstances, the detection accuracy of the biological information detector is poor.

According to several modes of the present invention, it is possible to provide a biological information detector and a biological information measuring device in which the detection accuracy or the measurement accuracy can be improved.

Means Used to Solve the Above-Mentioned Problems

A first aspect of the present invention relates to a biological information detector, characterized in comprising: a light-emitting part subjected to emit a first light directed at a detection site of a test subject and a second light directed in a direction other than a direction of the test subject; a first reflecting part subjected to reflect the second light and directing the second light towards the detection site; a light-receiving part subjected to receive light having biological information, the light produced by the first light and the second light being reflected at the detection site; and a second reflecting part subjected to reflect the light having biological information from the detection site and directing the light having biological information towards the light-receiving part.

According to the first aspect of the present invention, the second light, which does not directly arrive at the detection site of the test subject (e.g. a user), also reaches the detection site via the first reflecting part. Therefore, the amount of light reaching the detected part increases, and the detection accuracy (i.e., signal-to-noise ratio) of the biological information detector improves.

According to a second aspect of the present invention, the light-emitting part may have: a first light-emitting surface for emitting the first light, the first light-emitting surface facing the detection site; and a second light-emitting surface for emitting the second light, the second light-emitting surface being a side surface of the first light-emitting surface; the first reflecting part may have a wall part surrounding the second light-emitting surface; and the wall part may have a first reflecting surface for reflecting the second light towards the detection site.

The wall part (i.e., the first reflecting part) surrounding the second light-emitting surface of the light-emitting part having the first reflecting surface thus increases the amount of light reaching the detection site, and the accuracy of the biological information detector further increases.

According to a third aspect of the present invention, the wall part may further have a second reflecting surface for reflecting light that has been reflected at a surface of the test subject and does not contain biological information, thereby suppressing the light not having biological information from being incident on the light-receiving part.

The second reflecting surface of the first reflecting part is thus capable of minimizing incidence of light not having biological information (i.e., invalid light) onto the light-receiving part and improve the S/N (i.e., signal-to-noise ratio).

According to a fourth aspect of the present invention, the first reflecting part may project further towards the detection site than the light-receiving part.

Specifically, the shortest distance between the first reflecting part and the surface of the test subject may be smaller than the shortest distance between the light-emitting part and the surface of the test subject. The first reflecting part may thus project towards the detection site by e.g. a predetermined height $\Delta h1$ in relation to a surface of the light-emitting part that determines the shortest distance relative to the surface of the test subject (e.g. the first light-emitting surface). Specifically, a spacing between the first reflecting part and the surface of the test subject (e.g. $\Delta h2 = \Delta h0 - \Delta h1$) may be smaller than a spacing that represents the shortest distance between the light-receiving part and the surface of the test subject (e.g. $\Delta h0 = \Delta h1 + \Delta h2$). Therefore, in the first reflecting part, the presence of e.g. a projection $\Delta h1$ from the light-emitting part makes it possible to increase the area of the first reflecting surface and increase the amount of light reaching the detection site. Also, with regards to the light reflected at the detection site, the presence of e.g. $\Delta h2$ makes it possible to obtain a light path for the light to reach the second reflecting part from the detection site. Also, in an instance in which the first reflecting part has the second reflecting surface, adjusting $\Delta h1$ and $\Delta h2$ allows the amount of light having biological information (i.e., valid light) and light not having biological information (i.e., invalid light: noise) incident on the light-receiving part to be respectively adjusted, thereby making it possible to further improve the S/N.

According to a fifth aspect of the present invention, the biological information detector may further comprise a substrate having a first surface, and a second surface facing the first surface; wherein the light-receiving part may be positioned on the first surface; the first reflecting part may be positioned on the second surface; and an equation W1≤W2 may be satisfied, when, in a cross-sectional view, W1 is a maximum value for the length of the first reflecting part in a direction parallel to the first surface, and W2 is a maximum value for the length of the light-receiving part in the direction parallel to the first surface.

Having the maximum value W1 for the length of the first reflecting part be equal to or smaller than the maximum value W2 for the length of the light-receiving part thus makes it possible to increase the valid amount of light reaching the second reflecting part. Specifically, the maximum value W1 for the length of the first reflecting part may be set so that the first reflecting part does not block or reflect light reflected at the detection site (i.e., reflected light having biological information).

According to a sixth aspect of the present invention, a reflecting surface of the second reflecting part may be a spherical surface or a parabolic surface, wherein a center of an arc defining the spherical surface may be within the test subject, or a focus of a parabolic line defining the parabolic surface may be towards the test subject relative to a light-receiving surface of the light-receiving part.

In an instance in which the detection site is within the test subject, light reflected at the surface of the test subject does not contain biological information. The inventors identified that the second reflecting part minimizes light reflected at the surface of the test subject (or in a broader sense, noise) in an instance in which the center of the arc defining the spherical surface is within the test subject. Also, in an instance in which the reflecting surface of the second reflecting part is a parabolic surface, and the focus of the parabolic line defining the parabolic surface is towards the test subject relative to the light-receiving surface of the light-receiving part, there is a greater likelihood of light having a path that is nearly perpendicular to the surface of the test subject (e.g. the reflected first light; valid light) collecting on the light-receiving surface of the light-receiving part.

According to a seventh aspect of the present invention, the biological information detector may further contain a wristband capable of attaching the biological information detector to an arm of the test subject.

The detection site can thus be set on the arm of the test subject (i.e., the user). In other words, the biological information detector whose detection accuracy has been improved can be applied in an environment in which there is a significant level of noise arising from external light.

An eighth aspect of the present invention relates to a biological information measuring device, characterized in comprising: the biological information detector described above; and a biological information measuring part for measuring biological information from a light reception signal generated at the light-receiving part.

According to the eighth aspect of the present invention, the biological information detector whose detection accuracy has been improved can be used to increase the measurement accuracy of the biological information measuring device.

BRIEF DESCRIPTION OF THE DRAWINGS

FIGS. 2(A), 2(B), and 2(C) are examples of configurations of a first reflecting part;

FIGS. 3(A) and 3(B) are examples of the outer appearance of the first reflecting part and a light-emitting part;

DESCRIPTION OF EXEMPLARY EMBODIMENTS

A description shall now be given for the present embodiment. The present embodiment described below is not intended to unduly limit the scope of the Claims of the present embodiment. Not every configuration described in the present embodiment is necessarily an indispensable constituent feature of the present invention.

1. Biological Information Detector

Figure 1:
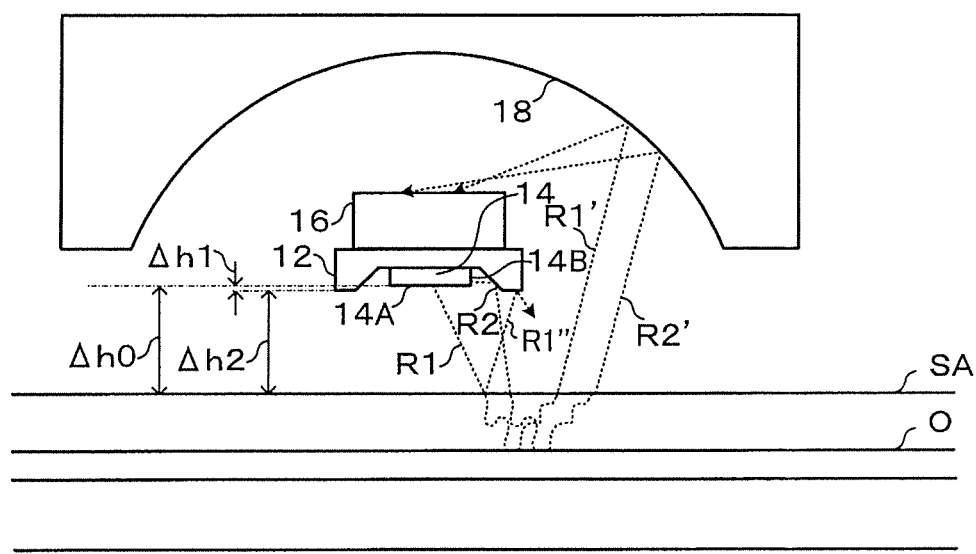
FIG. 1 is an example of a configuration of a biological information detector according to a present embodiment.

FIG. 1 shows an example of a configuration of a biological information detector according to the present embodiment. As shown in FIG. 1, the biological information detector contains a light-emitting part 14, a first reflecting part 12, a light-receiving part 16, and a second reflecting part 18. The light-emitting part 14 generates a first light R1 directed at a detection site O of a test subject (e.g. a user), and a second light R2 directed at a direction other than a direction of the detection site O (i.e., directed at the first reflecting part 12). The first reflecting part 12 reflects the second light R2 and directs the second light R2 towards the detection site O. The light-receiving part 16 receives lights R1', R2' (i.e., reflected lights), having biological information, the lights R1', R2' produced by each of the first light R1 and the second light R2 being reflected at the detection site O. The second reflecting part 18 reflects the lights R1', R2' having biological information from the detection site O (i.e. the reflected lights) and directs the lights R1', R2' towards the light-receiving part 16. The presence of the first reflecting part 12 causes the light second light R2, that does not directly reach the detection site O of the test subject (i.e., the user), to reach the detection site O. In other words, the amount of light reaching the detection site O via the first reflecting part 12 increases, and the efficiency of the light-emitting part 14 increases. Therefore, the detection accuracy (i.e., the signal-to-noise ratio) of the biological information detector increases.

In Patent Citation 1, there is disclosed a configuration corresponding to the second reflecting part 18 (i.e., a reflecting part 131 in FIG. 16 of Patent Citation 1). Specifically, the light-receiving part 12 in FIG. 16 of Patent Citation 1 receives light reflected at a detection site via the reflecting part 131. However, in Patent Citation 1, a configuration corresponding to the first reflecting part 12 is not disclosed. In other words, at the time of filing, those skilled in the art had not been aware of the issue of increasing the efficiency of the light-emitting part 11 in FIG. 16 in Patent Citation 1.

In the example shown in FIG. 1, the detection site O (e.g. a blood vessel) is within the test subject. As shown in FIG. 1, the light-emitting part 14 may have a first light-emitting surface 14A for emitting the first light R1, the first light-emitting surface 14A facing the detection site O. The first light R1 travels into the test subject and diffuses or scatters at the epidermis, the dermis, and the subcutaneous tissue. The first light R1 then reaches the detection site O, and is reflected at the detection site O. The reflected light R1' reflected at the detection site O diffuses or scatters at the subcutaneous tissue, the dermis, and the epidermis, and travels to the second reflecting part 18. The first light R1 is also partially absorbed at the blood vessel (or in a broader sense, the detection site O). Therefore, due to an effect of a pulse, the rate of absorption at the blood vessel varies, and the amount of the reflected light R1' reflected at the detection site O also varies. Biological information (e.g. pulse rate) is thus reflected in the reflected light R1' reflected at the detection site O.

In the example shown in FIG. 1, the light-emitting part 14 may also have a second light-emitting surface 14B for emitting the second light R2, the second light-emitting surface 14B being a side surface of the first light-emitting surface 14A. In such an instance, the first reflecting part 12 may have a wall part surrounding the second light-emitting surface 14B, and the wall part may have a first reflecting surface (corresponding to label 12-2 shown in FIGS. 2(A) through 2(C)) capable of reflecting the second light R2 towards the detection site O. The second light R2 is not necessarily limited to that emitted from the second light-emitting surface 14B. Specifically, the first reflecting surface (label 12-2 shown in FIGS. 2(A) through 2(C)) reflects light other than light travelling directly from the light-emitting part 14 to the detection site O (i.e., the second light R2) and directs the second light R2 towards the detection site O.

The second light R2 also travels into the test subject, and the reflected light R2' reflected at the detection site O travels towards the second reflecting part 18. Biological information (i.e., the pulse rate) is also reflected in the reflected light R2' reflected at the detection site O. In the example shown in FIG. 1, the first light R1 is partially reflected at a surface SA of the test subject (e.g. a skin surface). In an instance in which the detection site O is within the test subject, biological information (i.e., the pulse rate) is not reflected in reflected light R1" reflected at the surface SA of the test subject (i.e., a directly reflected light).

The wall part of the first reflecting part 12 may further have a second reflecting surface (corresponding to 12-3 in FIGS. 2(A) and 2(C)) for reflecting light not having biological information (i.e., invalid light; noise) reflected at the surface of the test subject, thereby minimizing incidence of light not having biological information onto the light-receiving part.

Examples of configurations of the biological information detector are not limited by that shown in FIG. 1, and the shape, or a similar attribute, of a part of the example of configuration (e.g. the first reflecting part 12) may be modified. The biological information may also be blood oxygen saturation level, body temperature, heart rate, or a similar variable; and the detection site O may be positioned at the surface SA of the test subject. In the example shown in FIG. 1, each of the first light R1 and the second light R2 is shown by a single line; however, in reality, the light-emitting part 14 emits many light beams in a variety of directions.

The light-emitting part 14 is, for example, an LED. The light emitted by the LED has a maximum intensity (or in a broader sense, a peak intensity) within a wavelength range of e.g. 425 nm to 625 nm, and is e.g. green in color. The thickness of the light-emitting part 14 is e.g. 20 μm to 1000 μm.

The light-receiving part 16 is e.g. a photodiode, and can generally be formed by a silicon photodiode. The thickness of the light-receiving part 16 is e.g. 20 μm to 1000 μm. The silicon photodiode has a maximum sensitivity (or in a broader sense, a peak sensitivity) for received light having a wavelength within a range of e.g. 800 nm to 1000 nm. Ideally, the light-receiving part 16 is formed by a gallium arsenide phosphide photodiode, and the gallium arsenide phosphide photodiode has a maximum sensitivity (or in a broader sense, a peak sensitivity) for received light having a wavelength within a range of e.g. 550 nm to 650 nm. Since biological substances (water or hemoglobin) readily allow transmission of infrared light within a wavelength range of 700 nm to 1100 nm, the light-receiving part 16 formed by the gallium arsenide phosphide photodiode is more capable of reducing noise components arising from external light than the light-receiving part 16 formed by the silicon photodiode.

FIGS. 2(A), 2(B), and 2(C) respectively show an example of a configuration of the first reflecting part 12 shown in FIG. 1. As shown in FIG. 2(A), the first reflecting part 12 may have a support part 12-1 for supporting the light-emitting part 14, and an inner wall surface 12-2 and a top surface 12-3 of the wall part surrounding the second light-emitting surface 14B of the light-emitting part 14. In FIGS. 2(A) through 2(C), the light-emitting part 14 is omitted. In the example shown in FIG. 2(A), the first reflecting part 12 is capable of reflecting the second light R2 towards the detection site O off the inner wall surface 12-2 (see FIG. 1), and has the first reflecting surface on the inner wall surface 12-2. The thickness of the support part 12-1 is e.g. 50 μm to 1000 μm, and the thickness of the top surface 12-3 is e.g. 100 μm to 1000 μm. The first reflecting part 12 may not necessarily have the support part 12-1, and the light-emitting part 14 may be supported by a part other than the first reflecting part 12.

In the example shown in FIG. 2(A), the inner wall surface 12-2 has an inclined surface (12-2) which, with increasing distance in a width direction (i.e., a first direction) from a center of the first reflecting part 12, inclines towards the detection site O in a height direction (i.e., a direction that is orthogonal with the first direction), in cross-section view. The inclined surface (12-2) in FIG. 2(A) is formed by, in cross-section view, an inclined plane, but may also be a curved surface shown in e.g. FIG. 2(C), or a similar inclined surface. The inner wall surface 12-2 may also be formed as a plurality of inclined flat surfaces whose angle of inclination vary from one another, or by a curved surface having a plurality of curvatures. In an instance in which the inner wall surface 12-2 of the first reflecting part 12 has an inclined surface, the inner wall surface 12-2 of the first reflecting part 12 is capable of reflecting the second light R2 towards the detection site O. In other words, the inclined surface on the inner wall surface 12-2 of the first reflecting part 12 can be said to be the first reflecting surface for improving the directivity of the light-emitting part 14. In such an instance, the amount of light reaching the detection site O increases further. The top surface 12-3 shown in FIGS. 2(A) and 2(C) may be omitted as shown, for example, in FIG. 2(B). In an instance in which the first reflecting part 12 has the top surface 12-3, the reflected light R1" reflected at the surface SA of the test subject (i.e., the directly reflected light) can be reflected towards the detection site O or surroundings thereof, and the reflected light R1" is deterred from reaching the light-receiving part 16 (see FIG. 1). Specifically, the top surface 12-3 shown in FIGS. 2(A) and 2(C) can be said to be the second reflecting surface for reflecting the directly reflected light (or in a broader sense, noise) that would otherwise reach the second reflecting part 18 and the light-receiving part 16, and reducing noise. In FIGS. 2(A) through 2(C), a range indicated by label 12-4 function as a mirror surface part.

In the example shown in FIG. 1, the first reflecting part 12 may project towards the detection site O by e.g. a predetermined height Δh1 (where Δh1 is e.g. 50 μm to 950 μm) in relation to a surface of the light-emitting part 14 that determines the shortest distance relative to the surface SA of the test subject (e.g. the first light-emitting surface 14A). In other words, a spacing between the first reflecting part 12 and the surface SA of the test subject (e.g. Δh2=Δh0−Δh1, where Δh2 is 200 μm to 1200 μm) may be smaller than a spacing that represents the shortest distance between the light-receiving part 14 and the surface SA of the test subject (e.g. Δh0=Δh1+Δh2). Therefore, in the first reflecting part 12, the presence of e.g. a projection Δh1 from the light-emitting part 14 makes it possible to increase the area of the first reflecting surface (12-2) and increase the amount of light reaching the detection site O. Also, with regards to the light reflected at the detection site O, the presence of a space Δh2 between the first reflecting part 12 and the surface SA of the test subject makes it possible to obtain a light path for the light to reach the second reflecting part 18 from the detection site O. Also, in an instance in which the first reflecting part 12 has the second reflecting surface (12-3), adjusting Δh1 and Δh2 allows the amount of light having biological information (i.e., valid light) and light not having biological information (i.e., invalid light: noise) incident on the light-receiving part 16 to be respectively adjusted, thereby making it possible to further improve the S/N.

FIGS. 3(A) and 3(B) respectively show an example of an outer appearance of the first reflecting part 12 and the light-emitting part 14 of FIG. 1 in plan view. In the example shown in FIG. 3(A), in plan view (when viewed from e.g. towards the detection site O shown in FIG. 1), an outer circumference of the first reflecting part 12 is circular, where the diameter of the circle is e.g. 200 μm to 11,000 μm. In the example shown in FIG. 3(A), the wall part (12-2) of the first reflecting part 12 surround the light-emitting part 14 (see FIGS. 1 and 2(A)). The outer circumference of the first reflecting part 12 may also be a quadrilateral (or specifically, a square) in plan view as shown e.g. in FIG. 3(B). Also, in the examples shown in FIGS. 3(A) and 3(B), in plan view (when viewed from e.g. towards the detection site O shown in FIG. 1), the outer circumference of the light-emitting part 14 is a quadrilateral (or specifically, a square), where the length of one side of the square is e.g. 100 μm to 10,000 μm. The outer circumference of the light-emitting part 14 may also be circular.

The first reflecting part 12 is made of metal whose surface is subjected to mirror surface finishing, and thereby has a reflective structure (or specifically, a mirror reflection structure). The first reflecting part 12 may also be formed from e.g. a resin whose surface is subjected to mirror surface finishing. Specifically, for example, a base metal forming a base of the first reflecting part 12 is readied, and a surface of the base metal is then e.g. subjected to plating. Alternatively, a mold of the first reflecting part 12 (not shown) is filled with a thermoplastic resin, molding is performed, and a metal film, for example, is then deposited by vapor deposition on a surface of the mold.

In the examples shown in FIGS. 3(A) and 3(B), in plan view (when viewed from e.g. towards the detection site O shown in FIG. 1), a region of the first reflecting part 12 other than that directly supporting the light-emitting part 14 (the inner wall surface 12-2 and the top surface 12-3, and a part of the support part 12-1) is exposed. The exposed region is shown as a mirror surface part 12-4 in FIG. 2(A). Although in the example shown in FIG. 2(A), a dotted line representing the mirror surface part 12-4 is shown within the first reflecting part 12, the mirror surface part 12-4 is actually formed on a surface of the first reflecting part 12.

In the examples shown in FIGS. 2(A), 2(B), and 2(C), the mirror surface part 12-4 preferably has a high reflectivity. The reflectivity of the mirror surface part 12-4 is e.g. 80% to 90% or higher. It is possible for the mirror surface part 12-4 to be formed only on the inclined surface of the inner wall surface 12-2. In an instance in which the mirror surface part 12-4 is formed not only on the inclined surface of the inner wall surface 12-2 but also on the support part 12-1, the directivity of the light-emitting part 14 increases further. In an instance in which the mirror surface part 12-4 is formed on the top surface 12-3, the first reflecting part 12 is capable of reflecting the reflected light R1", which has been reflected in the surface SA of the test subject (i.e., the directly reflected light; invalid light), towards the detection site O or the surroundings thereof, as shown e.g. on FIG. 1, and the reflected light R1" is deterred from reaching the second reflecting part 18 and the light-receiving part 16. Since the directivity of the light-emitting part 14 increases and the directly reflected light (or in a broader sense, noise) decreases, the detection accuracy of the biological information detector increases.

Figure 4:
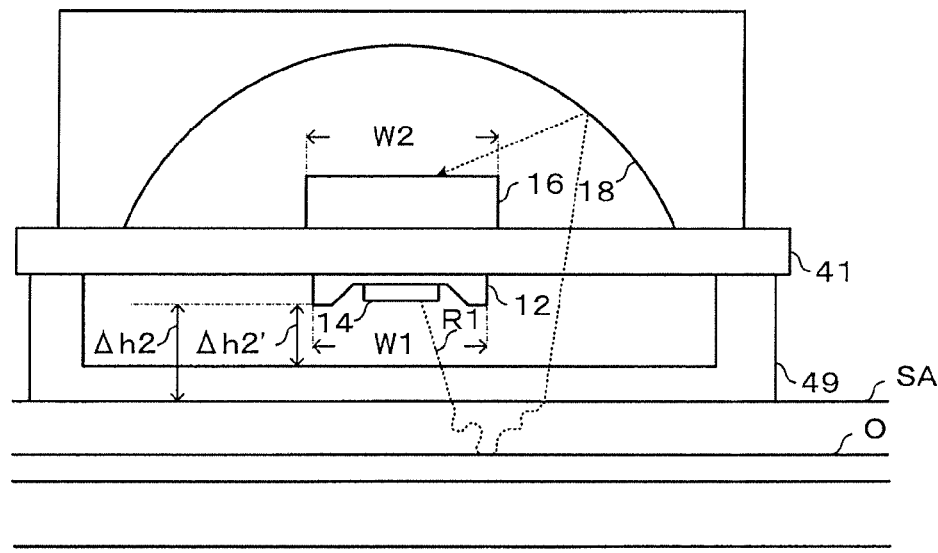
FIG. 4 is another example of a configuration of the biological information detector according to the present embodiment.

FIG. 4 shows another example of a configuration of the biological information detector according to the present embodiment. As shown in FIG. 4, the biological information detector may further comprise a substrate 41 having a first surface (e.g. a front surface) and a second surface that is opposite the first surface (e.g. a reverse surface). Structures that are identical to those in the example described above are affixed with the same numerals, and a description of the structures will be omitted. In the example shown in FIG. 4, the light-receiving part 16 is positioned on the first surface, and the first reflecting part 12 is positioned on the second surface. When, in cross-section view, W1 is a maximum value for the length of the first reflecting part 12 in a direction parallel to the first surface, and W2 is a maximum value for the length of the light-receiving part 16 in the same direction, an equation W1≤W2 is satisfied.

The substrate 41 is formed of e.g. a transparent material (e.g. polyimide) and allows transmission of the reflected light R1' produced by the first light R1 emitted at the detection site O, and other light. The maximum value W1 for the length of the first reflecting part 12 is made equal to or less than the maximum value W2 for the length of the light-receiving part 16, thereby making it possible to increase the amount of light reaching the second reflecting part 18. In other words, the maximum value W1 for the length of the first reflecting part 12 can be set so that the first reflecting part 12 does not block or reflect the reflected light R1' reflected at the detection site O. The thickness of the substrate 41 is e.g. 10 μm to 1000 μm. Wiring for the light-emitting part 14 and wiring for the light-receiving part 16 may be formed on the substrate 41. The substrate 41 is e.g. a printed circuit board; however, a printed circuit board is not generally formed from a transparent material, as with the substrate 15 of Patent Citation 1. Specifically, the inventors purposefully used a configuration in which the printed circuit board is formed from a material that is transparent at least with respect to the emission wavelength of the light-emitting part 14.

In the example shown in FIG. 4, the second light R2 emitted at the detection site O via the first reflecting part 12, the reflected light R2' reflected at the detection site O, and the reflected light R1" reflected at the surface SA of the test subject (i.e., the directly reflected light) are omitted (refer to FIG. 1). Those skilled in the art should be readily able to understand the path of the second light R2 and the accurate path of the first light R1.

As shown in FIG. 4, the biological information detector may further contain a protecting part 49 for protecting the first reflecting part 12 and the light-emitting part 14. The protecting part 49 is formed from e.g. a transparent material (e.g. glass), and allows transmission of the first light R1 emitted at the detection site O, the reflected light R1' produced by the first light R1 being reflected, and other light. The protecting part 49 also makes it possible to ensure that there is a gap between the first reflecting part 12 and the detection site O (e.g. Δh2). There also exists a gap between the first reflecting part 12 and the protecting part 49 (e.g. Δh2'). The thickness of the protecting part 49 is e.g. 1 μm to 1000 μm.

The substrate 41 is held between the second reflecting part 18 and the protecting part 49; the light-receiving part 16 is placed on the substrate 41 towards the second reflecting part 18 (or specifically, on the first surface of the substrate 41); and the light-emitting part 14 is placed on the substrate 41 towards the protecting part 49 (or specifically, on the second surface of the 41). Since the substrate 41 is held between the second reflecting part 18 and the protecting part 49, even when the light-emitting part 14 and the light-receiving part 16 are positioned on the substrate 41, there is no need to separately provide a mechanism for supporting the substrate 41 itself, and the number of components is smaller. Also, since the substrate 41 is formed from a material that is transparent with respect to the emission frequency, the substrate 41 can be disposed on a light path from the light-emitting part 14 to the light-receiving part 16, and there is no need to accommodate the substrate 41 at a position away from the light path, such as within the second reflecting part 18. A biological information detector that can be readily assembled can thus be provided.

Figure 5:
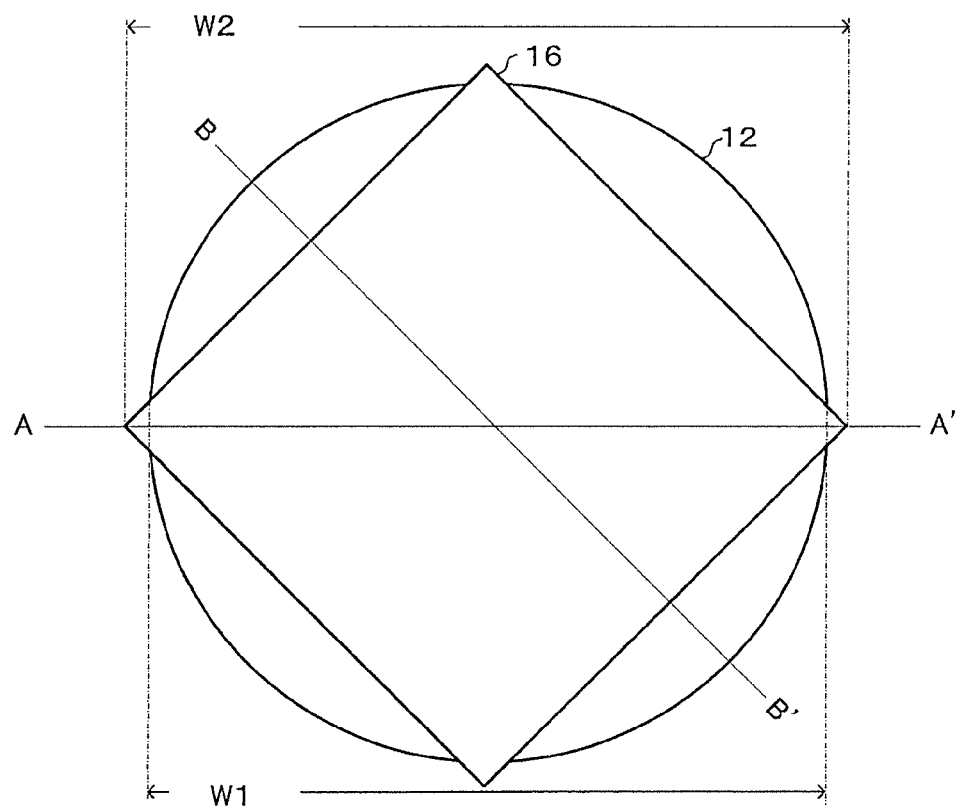
FIG. 5 is an example of an outer appearance of a light-receiving part.

FIG. 5 shows an example of an outer appearance of the light-receiving part 16 in FIG. 4. In the example shown in FIG. 5, in plan view (e.g. when viewed from a side towards the second reflecting part 18 in FIG. 4), an outer circumference of the light-receiving part 16 is a quadrilateral (or specifically, a square), and one side of the square is e.g. 100 μm to 10,000 μm. An outer circumference of the first reflecting part 12 is, in plan view (e.g. when viewed from a side towards the second reflecting part 18 in FIG. 4), circular. The outer circumference of the first reflecting part 12 may instead be a quadrilateral (or specifically, a square), as in the example shown in FIG. 3(B). The outer circumference of the light-receiving part 16 may also be circular.

In the example shown in FIG. 5, as shown by line segment A-A', when W1 is a maximum value for the length of the first reflecting part 12 and W2 is a maximum value for the length of the light-receiving part 16, an equation W1≤W2 is satisfied. A cross-section view along the line segment A-A' in FIG. 5 corresponds to FIG. 4. A cross-section view along line segment B-B' in FIG. 5 resembles FIG. 1, and the maximum value W1 of the length of the first reflecting part 12 is larger than a minimum value of the length of the light-receiving part 16. Although the maximum value W1 of the length of the first reflecting part 12 may be set so as to be equal to or smaller than the minimum value of the length of the light-receiving part 16, the efficiency of the first reflecting part 12 (or, in a broader sense, the efficiency of the light-emitting part 14) would decrease. In the example shown in FIG. 5, the maximum value W1 of the length of the first reflecting part 12 is set to be equal to or smaller than the maximum value W2 of the length of the light-receiving part 16, and the maximum value W1 of the length of the first reflecting part 12 is set to be larger than the minimum value of the length of the light-receiving part 16, so that the efficiency of the light-emitting part 14 can be maintained without blocking or reflecting the reflected light R1'.

Figure 6:
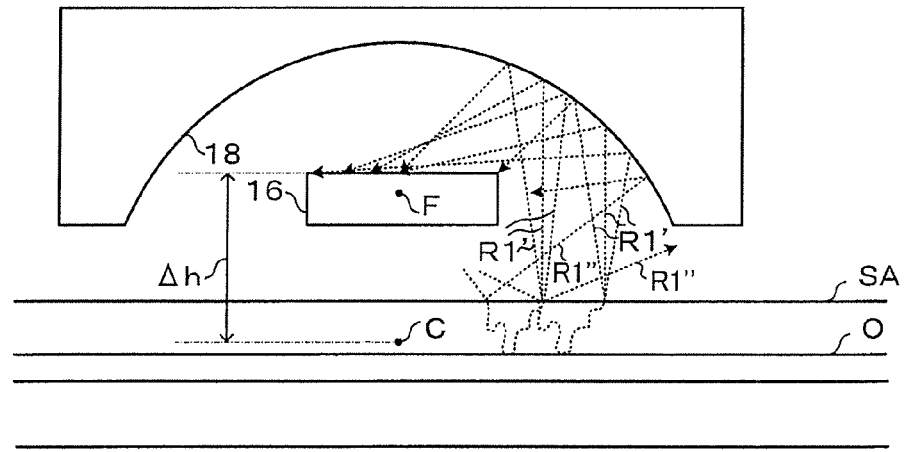
FIG. 6 is a schematic diagram showing a setting position of the second reflecting part.

FIG. 6 is a schematic diagram showing a setting position of the second reflecting part 18 in FIG. 1 or 4. The reflecting surface of the second reflecting part 18 may be formed as e.g. a spherical surface (or in a broader sense, a dome surface), so that the reflected light R1', produced by the first light R1 being reflected at the detection site O, is reflected towards the light-receiving part 16. As shown in FIG. 6, in cross-section view, the reflecting surface of the second reflecting part 18 is an arc. The radius of the arc is e.g. 1000 μm to 15,000 μm. A center C of the arc that defines the spherical surface is located within the test subject. In an instance in which the detection site O is located within the test subject, the reflected light R1" reflected at the surface SA of the test subject is an invalid light not having biological information. The inventors identified that in an instance in which the reflecting surface of the second reflecting part 18 is formed by a spherical surface and the center C of the arc that defines the spherical surface, the second reflecting part 18 minimizes reflected light reflected at the surface SA of the test subject (or in a broader sense, noise). In FIG. 6, the distance between the light-receiving surface of the light-receiving part 16 and the center C of the arc that defines the spherical surface is represented by Δh.

The reflecting surface of the second reflecting part 18 may also be formed by a parabolic surface (or in a broader sense, a dome surface) instead of the spherical surface. As shown in FIG. 6, in cross-section view, the reflecting surface of the second reflecting part 18 is an arc, but may be a parabolic line instead of an arc. If the reflecting surface of the second reflecting part 18 is a parabolic surface, the focus of the parabolic line defining the parabolic surface is shown in FIG. 6 by the letter F. The focus F of the parabolic line defining the parabolic surface is located towards the test subject relative to the light-receiving surface of the light-receiving part 16. Light that travels perpendicular to the surface SA of the test subject reflects at the reflecting surface of the second reflecting part 18 (i.e., the parabolic surface) and collects at the focus F of the parabolic line defining the parabolic surface. Therefore, the focus F being located so as to not coincide with the light-receiving surface of the light-receiving part 16 results in a greater likelihood of light having a path that is nearly perpendicular to the surface SA of the test subject (e.g. the reflected light R1' produced by reflection of the first light R1; valid light) collecting on the light-receiving surface of the light-receiving part 16.

The second reflecting part 18 is formed from e.g. a resin, whose surface (i.e., the reflecting surface facing the light-receiving part 16) is subjected to mirror surface finishing, and thereby has a reflective structure (or specifically, a mirror reflection structure). In other words, the second reflecting part 18 is capable of causing mirror reflection of light without causing diffuse reflection of light. In an instance in which the second reflecting part 18 has a mirror reflection structure, the second reflecting part 18 is also capable of not causing the reflected light R1" (i.e., the directly reflected light) to reflect towards the light-receiving part 16, where the reflected light R1" produced by reflection of the first light R1 has a reflection angle that is different to that of the reflected light R1' produced by reflection of the first light R1. In such an instance, the detection accuracy of the biological information detector further increases. As shown in FIG. 6, since the reflected light R1' produced by reflection of the first light R1 originates from the detection site O that is within the test subject, the reflection angle of the reflected light R1' produced by reflection of the first light R1 (i.e., a reflection angle relative to a straight line perpendicular to the surface SA of the test subject) is generally small. Meanwhile, since the reflected light R1" produced by reflection of the first light R1 originates from the surface SA of the test subject, the reflection angle of the reflected light R1" produced by reflection of the first light R1 is generally large.

In FIG. 16 of Patent Citation 1, there is disclosed a reflecting part 131, and according to paragraphs [0046], [0059], and [0077] in Patent Citation 1, the reflecting part 131 has a diffuse reflection structure, and the reflectivity is increased to increase the efficiency of the first reflecting part 12. However, at the time of filing, it had not been recognized by those skilled in the art that in the reflecting part 131 according to Patent Citation 1, directly reflected light (or in a broader sense, noise) is also reflected towards the first reflecting part 12. In other words, the inventors identified that reducing a noise component arising from the directly reflected light from a light reception signal increases the efficiency of the light-receiving part. Specifically, the inventors identified that the detection accuracy of the biological information detector is further increased in an instance in which the second reflecting part 18 has a mirror reflection structure.

Figure 7:
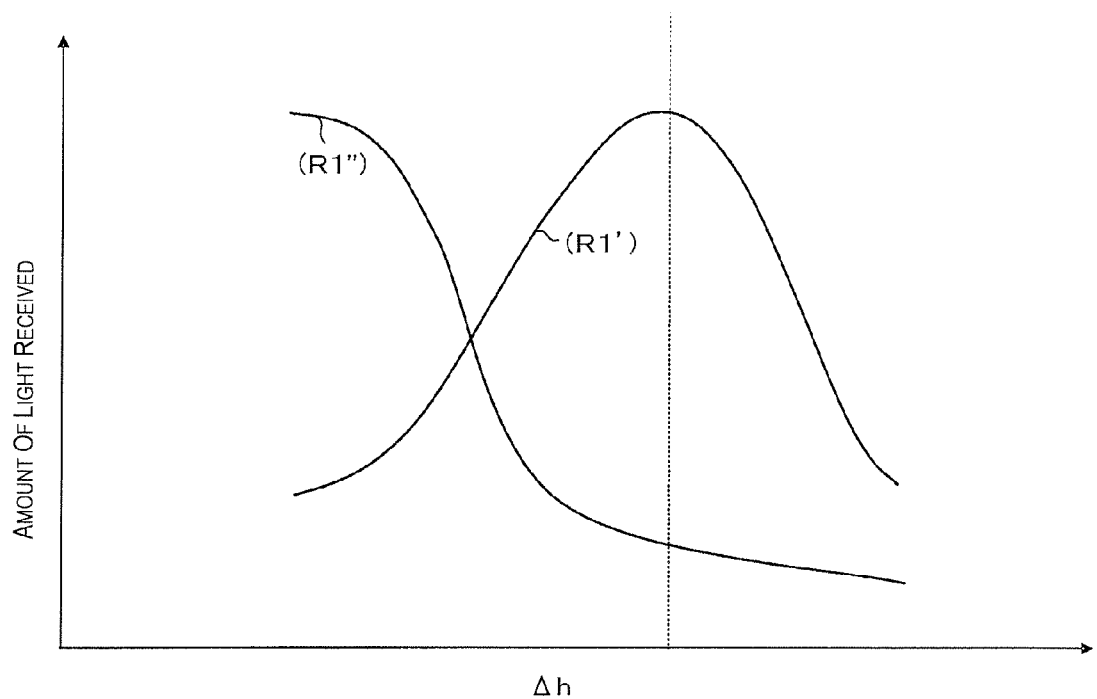
FIG. 7 is a diagram showing a relationship between the setting position of the second reflecting part and the amount of light received at the light-receiving part.

FIG. 7 is a diagram showing a relationship between the setting position of the second reflecting part 18 and the amount of light received at the light-receiving part 16 in FIG. 6. As shown in FIG. 7, with increasing distance Δh between the light-receiving surface of the light-receiving part 16 and the center C of the arc defining the spherical surface, the amount of directly reflected light reflected at the surface SA of the test subject (or, in a broader sense, noise corresponding to the reflected light R1", for example) decreases, while light reflected at the detection site O (or, in a broader sense, biological information corresponding to reflected light R1', for example) increases and then decreases. The position of the Δh can accordingly be optimized. In an instance in which the reflecting surface of the second reflecting part 18 is a parabolic surface, the distance between the light-receiving part of the light-receiving part 16 and the focus F of the parabolic line defining the parabolic surface can also be optimized.

2. Biological Information Measuring Device

Figure 8:
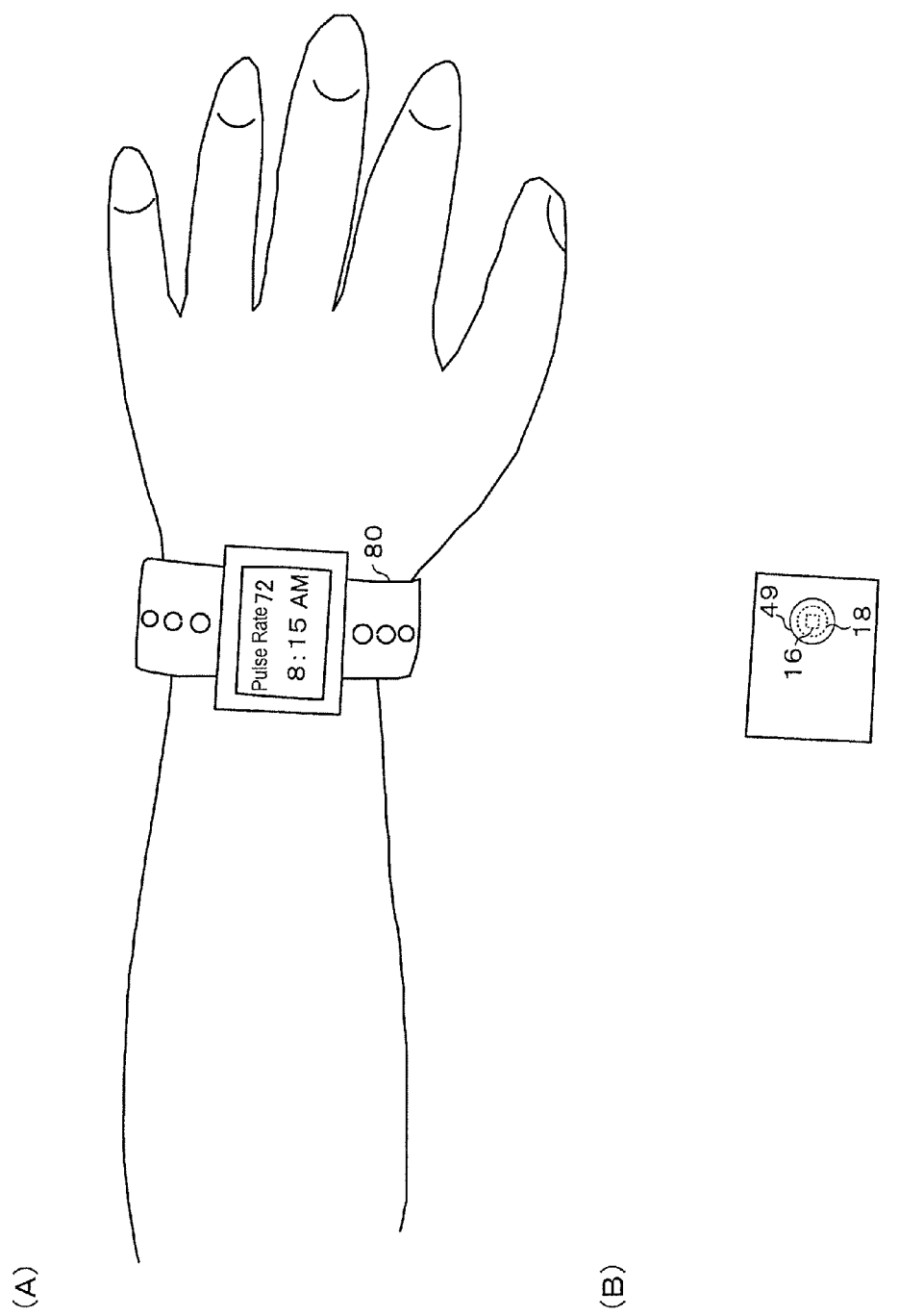
FIGS. 8(A) and 8(B) are examples of the outer appearance of a biological information measuring device containing the biological information detector.

FIGS. 8(A) and 8(B) are examples of outer appearances of a biological information measuring device containing the biological information detector such as that shown in FIG. 1. As shown in FIG. 8(A), the biological information detector shown in FIG. 1, for example, may further contain a wristband 80 capable of attaching the biological information detector to an arm (or specifically, a wrist) of the test subject (i.e., the user). In the example shown in FIG. 8(A), the biological information is the pulse rate indicated by e.g. "72." The biological information detector is installed in a watch showing the time (e.g. "8:15 am"). As shown in FIG. 8(B), an opening part is provided to a back cover of the watch, and the protecting part 49 shown in FIG. 4, for example, is exposed in the opening part. In the example shown in FIG. 8(B), the second reflecting part 18 and the light-receiving part 16 are installed in a watch. In the example shown in FIG. 8(B), the first reflecting part 12, the light-emitting part 14, the wristband 80, and other components are omitted.

Figure 9:
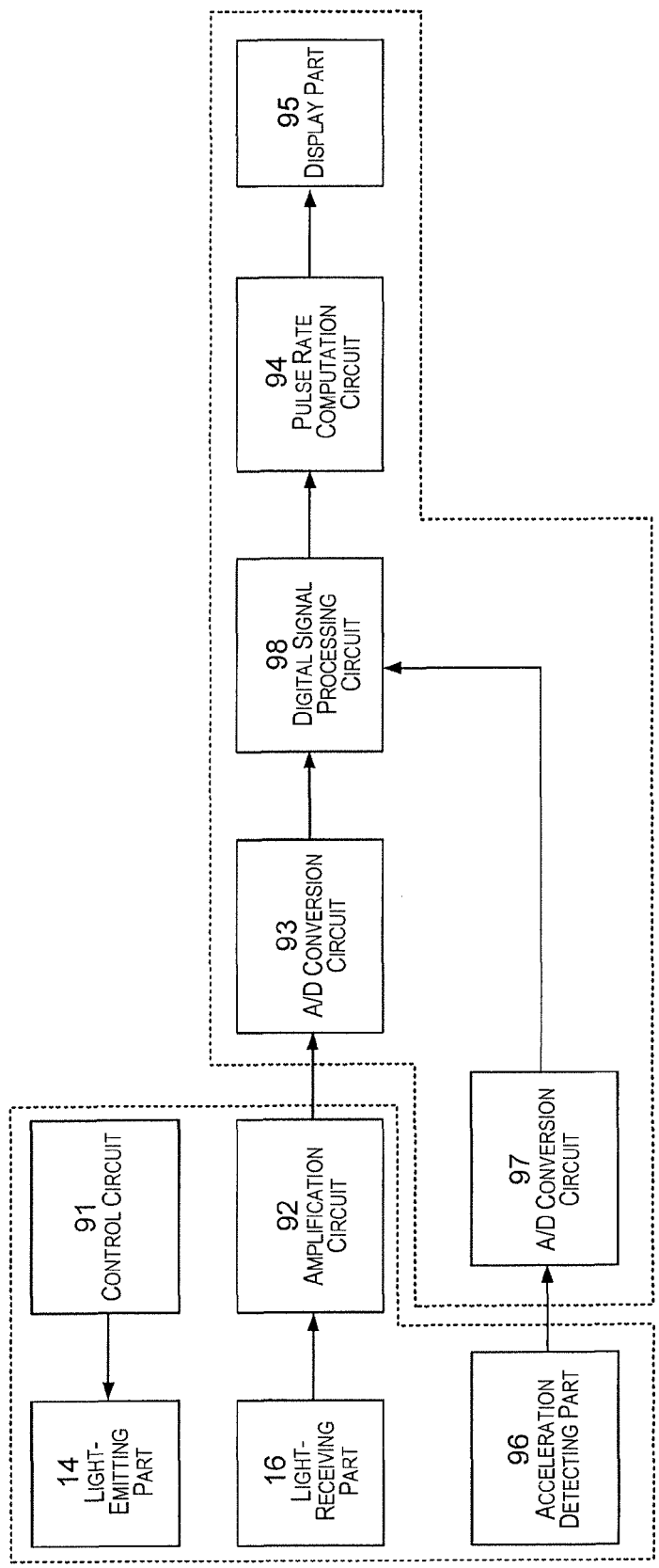
FIG. 9 is an example of a configuration of the biological information measuring device.

FIG. 9 is an example of a configuration of the biological information measuring device. The biological information measuring device includes the biological information detector as shown e.g. in FIG. 1, and a biological information measuring part for measuring biological information from a light reception signal generated at the light-receiving part 16 of the biological information detector. As shown in FIG. 9, the biological information detector may have a light-emitting part 14 and a control circuit 91 for controlling the light-emitting part 14. The biological information detector may further have an amplification circuit 92 for amplifying the light reception signal from the light-receiving part 16. The biological information measuring part may have an A/D conversion circuit 93 for performing A/D conversion of the light reception signal from the light-receiving part 16, and a pulse rate computation circuit 94 for computationally obtaining the pulse rate. The biological information measuring part may further have a display part 95 for displaying the pulse rate.

The biological information detector may have an acceleration detecting part 96, and the biological information measuring part may further have an A/D conversion circuit 97 for performing A/D conversion of a light reception signal from the acceleration detecting part 96 and a digital signal processing circuit 98 for processing a digital signal. The configuration of the biological information measuring device is not limited to that shown in FIG. 9. The pulse rate computation circuit 94 in FIG. 9 may be e.g. an MPU (i.e., a micro processing unit) of an electronic device installed with the biological information detector.

The control circuit 91 in FIG. 9 drives the light-emitting part 14. The control circuit 91 is e.g. a constant current circuit, delivers a predetermined voltage (e.g. 6 V) to the light-emitting part 14 via a protective resistance, and maintains a current flowing to the light-emitting part 14 at a predetermined value (e.g. 2 mA). The control circuit 91 is capable of driving the light-emitting part 14 in an intermittent manner (e.g. at 128 Hz) in order to reduce consumption current. The control circuit 91 is formed on e.g. a motherboard, and wiring between the control circuit 91 and the light-emitting part 14 is formed e.g. on the substrate 41 shown in FIG. 4.

The amplification circuit 92 shown in FIG. 9 is capable of removing a DC component from the light reception signal (i.e., an electrical current) generated in the light-receiving part 16, extracting only an AC component, amplifying the AC component, and generating an AC signal. The amplification circuit 92 removes the DC component at or below a predetermined wavelength using e.g. a high-pass filter, and buffers the AC component using e.g. an operational amplifier. The light reception signal contains a pulsating component and a body movement component. The amplification circuit 92 and the control circuit 91 are capable of feeding a power supply voltage for operating the light-receiving part 16 at e.g. reverse bias to the light-receiving part 16. In an instance in which the light-emitting part 14 is intermittently driven, the power supply to the light-receiving part 16 is also intermittently fed, and the AC component is also intermittently amplified. The amplification circuit 92 is formed on e.g. the mother board, and wiring between the amplification circuit 92 and the light-receiving part 16 is formed on e.g. the substrate 41 shown in FIG. 4. The amplification circuit 92 may also have an amplifier for amplifying the light reception signal at a stage prior to the high-pass filter. In an instance in which the amplification circuit 92 has an amplifier, the amplifier is formed e.g. on the substrate 41 shown in FIG. 4.

The A/D conversion circuit 93 shown in FIG. 9 converts an AC signal generated in the amplification circuit 92 into a digital signal (i.e., a first digital signal). The acceleration detecting part 96 shown in FIG. 9 calculates e.g. gravitational acceleration in three axes (i.e., x-axis, y-axis, and z-axis) and generates an acceleration signal. Movement of the body (i.e., the arm), and therefore the movement of the biological information measuring device, is reflected in the acceleration signal. The A/D conversion circuit 97 shown in FIG. 9 converts the acceleration signal generated in the acceleration detecting part 96 into a digital signal (i.e., a second digital signal).

The digital signal processing circuit 98 shown in FIG. 9 uses the second digital signal to remove or reduce the body movement component in the first digital signal. The digital signal processing circuit 98 may be formed by e.g. an FIR filter or another adaptive filter. The digital signal processing circuit 98 inputs the first digital signal and the second digital signal into the adaptive filter and generates a filter output signal in which noise has been removed or reduced.

The pulse rate computation circuit 94 shown in FIG. 9 uses e.g. fast Fourier transform (or in a broader sense, discrete Fourier transform) to perform a frequency analysis on the filter output signal. The pulse rate computation circuit 94 identifies a frequency that represents a pulsating component based on a result of the frequency analysis, and computationally obtains a pulse rate.

Although a detailed description was made concerning the present embodiment as stated above, persons skilled in the art should be able to easily understand that various modifications are possible without substantially departing from the scope and effects of the present invention. Accordingly, all of such examples of modifications are to be included in the scope of the present invention. For example, terms stated at least once together with different terms having broader sense or identical sense in the specification or drawings may be replaced with those different terms in any and all locations of the specification or drawings.

The entire disclosure of Japanese Patent Application No. 2010-000453, filed Jan. 5, 2010 is expressly incorporated by reference herein.

What is claimed is:

1. A biological information detector, comprising:
   a light-emitting part configured to emit a first light directed at a detection site of a test subject and a second light directed in a direction other than a direction of the detection site;
   a first reflecting part configured to be disposed on a substrate and to reflect the second light and directing the second light towards the detection site, wherein the first reflecting part is disposed by a predetermined distance projecting from the light-emitting part toward the detection site; and
   a light-receiving part configured to be disposed on the substrate and to receive light having biological information, the light produced by the first light and the second light being reflected at the detection site,
   wherein an equation $W1 \leq W2$ is satisfied, when in a cross-sectional view, W1 is a maximum value for the length of the first reflecting part in a direction parallel to a first surface of the substrate, and W2 is a maximum value for the length of the light-receiving part in the direction parallel to the first surface.

2. The biological information detector according to claim 1, wherein
   the light-emitting part includes:
      a first light-emitting surface configured to emit the first light, the first light-emitting surface facing the detection site, and
      a second light-emitting surface configured to emit the second light, the second light-emitting surface being a side surface of the first light-emitting surface.

3. The biological information detector according to claim 1, wherein
   the light-emitting part is surrounded by the first reflecting part disposed on the substrate.

4. The biological information detector according to claim 1, wherein
   the first reflecting part projects further towards the detection site than the light-receiving part.

5. The biological information detector according to claim 1, wherein
   the W1 is a length of a diagonal line of the first reflecting part in a plan view.

6. The biological information detector according to claim 1, further comprising:
   a wristband capable of attaching the biological information detector to an arm of the test subject.

7. A biological information measuring device, comprising:
   the biological information detector according to claim 1, and
   a biological information measuring part configured to measure biological information from a light reception signal generated by the light-receiving part.

8. A biological information detector, comprising:
   a light-emitting part configured to emit a first light directed at a detection site of a test subject and a second light directed in a direction other than a direction of the detection site;
   a first reflecting part configured to be disposed on a substrate and to reflect the second light and directing the second light towards the detection site; and
   a light-receiving part configured to be disposed on the substrate and to receive the light having biological information, the light produced by the first light and the second light being reflected at the detection site, wherein
   an equation $W1 \leq W2$ is satisfied, when in a cross-sectional view, W1 is a maximum value for the length of the first reflecting part in a direction parallel to a surface of the substrate, and W2 is a maximum value for the length of the light-receiving part in the direction parallel to the surface.

9. The biological information detector according to claim 8, wherein
   the light-emitting part includes:
      a first light-emitting surface configured to emit the first light, the first light-emitting surface facing the detection site, and
      a second light-emitting surface configured to emit the second light, the second light-emitting surface being a side surface of the first light-emitting surface.

10. The biological information detector according to claim 8, wherein
    the light-emitting part is surrounded by the first reflecting part disposed on the substrate.

11. The biological information detector according to claim 8, wherein
    the first reflecting part projects further towards the detection site than the light-receiving part.

12. The biological information detector according to claim 8, wherein
    the W1 is a length of a diagonal line of the first reflecting part in a plan view.

13. The biological information detector according to claim 8, further comprising:
    a wristband capable of attaching the biological information detector to an arm of the test subject.

14. A biological information measuring device, comprising:
    the biological information detector according to claim 8, and
    a biological information measuring part configured to measure biological information from a light reception signal generated by the light-receiving part.

* * * * *